US010149951B2

(12) United States Patent
Hancock et al.

(10) Patent No.: US 10,149,951 B2
(45) Date of Patent: Dec. 11, 2018

(54) CONTROLLABLE RATE TURBULATING NOZZLE

(71) Applicant: Mystic Pharmaceuticals, Inc., Cedar Park, TX (US)

(72) Inventors: Jesse Ryan Hancock, Cedar Park, TX (US); Michael Shaw, Austin, TX (US)

(73) Assignee: Mystic Pharmaceuticals, Inc., Cedar Park, TX (US)

(*) Notice: Subject to any disclaimer, the term of this patent is extended or adjusted under 35 U.S.C. 154(b) by 348 days.

(21) Appl. No.: 14/515,489

(22) Filed: Oct. 15, 2014

(65) Prior Publication Data

US 2015/0101595 A1 Apr. 16, 2015

Related U.S. Application Data

(60) Provisional application No. 61/891,300, filed on Oct. 15, 2013.

(51) Int. Cl.
*A61M 15/00* (2006.01)
*A61F 9/00* (2006.01)
(Continued)

(52) U.S. Cl.
CPC ....... *A61M 15/0036* (2014.02); *A61F 9/0008* (2013.01); *A61M 15/0061* (2014.02);
(Continued)

(58) Field of Classification Search
CPC .. A61M 11/00; A61M 11/002; A61M 11/006; A61M 11/008; A61M 15/00; A61M 15/0028; A61M 15/003; A61M 15/0031; A61M 15/0033; A61M 15/0035; A61M 15/0036; A61M 15/0038; A61M 15/004; A61M 15/0061
See application file for complete search history.

(56) References Cited

U.S. PATENT DOCUMENTS 3,258,913 A * 7/1966 Moorehead ............ F02C 7/042 239/265.43
4,338,931 A * 7/1982 Cavazza ........... A61M 15/0028 128/203.15
(Continued)

FOREIGN PATENT DOCUMENTS

EP 1762265 A1 * 3/2007 ........ A61M 15/0028
EP 1844809 A1 10/2007

OTHER PUBLICATIONS

Machine translation of EP 1762265 A1.*
(Continued)

*Primary Examiner* — (Jackie) Tan-Uyen T Ho
*Assistant Examiner* — Joseph D Boecker
(74) *Attorney, Agent, or Firm* — Christopher Shay

(57) ABSTRACT

A piercing device for use in internally pierced blister delivery devices include a base, a piercer body and an internal fluid path. The internal fluid path includes one or more inlet channels into a central cavity which is connected to one or more delivery channels and exit ports. The cavity is defined by angular walls and top to create turbulence in the fluid flow and to produce a controllable spray, mist, drops, plume or stream delivery. The piercer body also provides a pointed lancet disposed in the center of the exit ports for piercing the lidstock of a formed blister.

31 Claims, 10 Drawing Sheets

Figure 1:
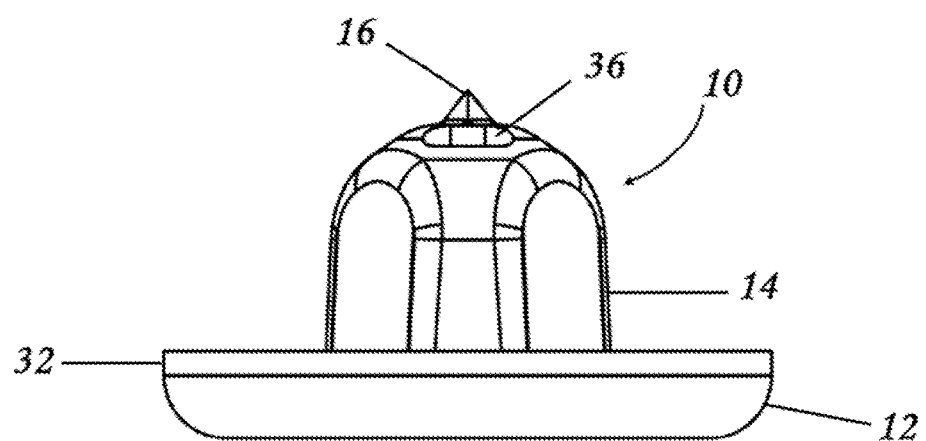
Figure 2:
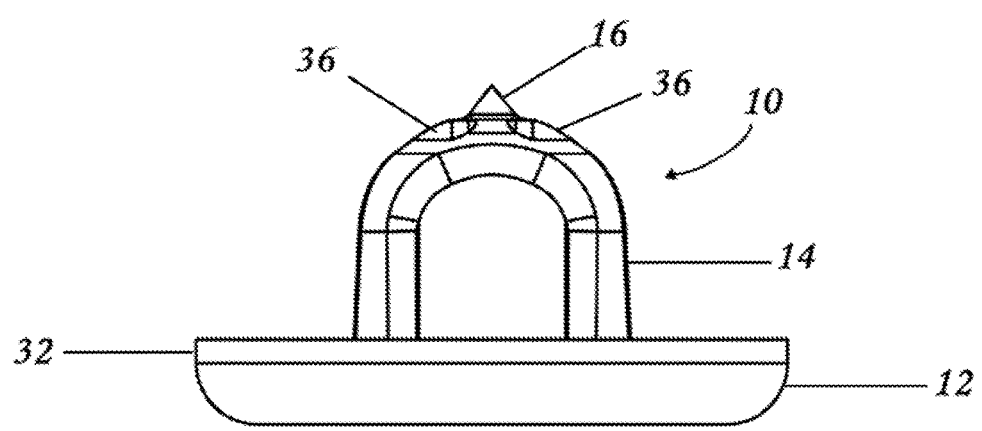

(51) Int. Cl.
*A61M 11/00* (2006.01)
*A61M 31/00* (2006.01)
*A61M 35/00* (2006.01)

(52) U.S. Cl.
CPC ......... *A61M 11/008* (2014.02); *A61M 35/003* (2013.01); *A61M 2202/04* (2013.01); *A61M 2202/064* (2013.01); *A61M 2210/04* (2013.01); *A61M 2210/0612* (2013.01); *A61M 2210/0618* (2013.01); *A61M 2210/0662* (2013.01)

(56) References Cited

U.S. PATENT DOCUMENTS

| | | | |
|---|---|---|---|
| 4,627,432 A | 12/1986 | Newell et al. | |
| 6,257,232 B1* | 7/2001 | Andersson | A61M 15/0065 128/203.15 |
| 6,520,179 B1* | 2/2003 | Von Schuckmann | A61M 15/0045 128/203.12 |
| 7,143,765 B2 | 12/2006 | Asking et al. | |
| 7,669,597 B2 | 3/2010 | Sullivan et al. | |
| 7,678,078 B1 | 3/2010 | Peyman et al. | |
| 8,585,659 B2 | 11/2013 | Shay | |
| 8,834,411 B2 | 9/2014 | Shay et al. | |
| 2004/0168687 A1* | 9/2004 | Asking | A61M 15/0045 128/203.15 |
| 2005/0238708 A1 | 10/2005 | Jones et al. | |
| 2006/0169278 A1* | 8/2006 | Djupesland | A61M 15/0028 128/200.14 |
| 2006/0202385 A1* | 9/2006 | Xu | A61M 37/0015 264/219 |
| 2007/0051362 A1 | 3/2007 | Sullivan et al. | |
| 2007/0221216 A1* | 9/2007 | Ganem | A61M 15/0028 128/203.12 |
| 2007/0221535 A1* | 9/2007 | Wachtel | A61M 15/0045 206/538 |
| 2008/0283439 A1* | 11/2008 | Sullivan | A61M 15/0028 206/531 |
| 2010/0108062 A1* | 5/2010 | Ganem | A61M 15/0028 128/203.21 |
| 2010/0331765 A1* | 12/2010 | Sullivan | A61M 15/08 604/24 |
| 2011/0048414 A1* | 3/2011 | Hoekman | A61M 15/00 128/200.23 |
| 2011/0056488 A1* | 3/2011 | Harmer | A61M 15/0028 128/200.23 |
| 2011/0220234 A1* | 9/2011 | Haas | A61M 15/0028 138/109 |
| 2012/0063961 A1* | 3/2012 | Chan | B01J 8/1827 422/140 |
| 2012/0074176 A1* | 3/2012 | Sullivan | A61M 15/0028 222/541.2 |
| 2013/0047985 A1* | 2/2013 | Harris | A61M 15/0028 128/203.15 |
| 2013/0187984 A1* | 7/2013 | Feinn | B41J 2/14016 347/47 |
| 2013/0327327 A1* | 12/2013 | Edwards | A61M 15/0028 128/203.11 |

OTHER PUBLICATIONS

International Search Report (PCT/US2014/060781) dated Dec. 31, 2014.
International Search Report (PCT/US2012/040006) dated Sep. 7, 2012.

* cited by examiner

SECTION B-B

SECTION A-A

SECTION C-C

SECTION D-D

SECTION E-E

CONTROLLABLE RATE TURBULATING NOZZLE

CROSS-REFERENCE TO RELATED APPLICATIONS

This application claims benefit of priority to U.S. Provisional Application No. 61/891,300, filed Oct. 15, 2013, the entire disclosure of which is incorporated herein by reference.

STATEMENT REGARDING FEDERALLY SPONSORED RESEARCH OR DEVELOPMENT

N/A

BACKGROUND OF THE INVENTION

There is a growing number of drugs, biologics, and liquids for which the most effective, or most convenient method of administration is by delivery of a spray or mist. A variety of devices are known for delivering a controlled amount of a pharmaceutical preparation in a spray, stream or mist to the nose, eye, ear, lungs, oral mucosal membranes, such as in the sublingual and buccal region, or throat of a user, or for topical delivery of an active agent. Various devices for nose to brain, systemic or topical delivery of a liquid or even a powdered formulation include a measured amount of a pharmaceutical composition contained in a crushable ampoule, blister or other dosage form that is forced against a penetrating device during use, to pierce the dosage form and release the contents.

The effectiveness of this type of dosage depends on the ability to deliver a precisely measured amount of active agent through a small opening with enough force and with control of the spray, stream or mist geometry to ensure that the correct amount of active agent reaches the desired target. This is of particular importance as more drugs and vaccines are being delivered to the eye, oral mucosal membranes, brain, nasal mucosa or to the lungs through the nasal passages. It is a further advantage if the active agents can be stored and delivered from the same dosage form without the risk of contamination prior to delivery.

SUMMARY

The present disclosure provides a delivery device for drugs, biologics, diagnostic reagents, pharmaceutical dosage forms or other active chemical agents for use in delivery devices that deliver a stream, drops, particles, spray or mist in a desired volume and spray geometry to a human or non-human animal. The dosage forms can be used, for example, to deliver a measured dose of a pharmaceutical, biologic or medical composition to the nasal passages, to the eye, to the mouth, into the ear, into the lungs, into the throat, to the brain, or to a topical location of a user. In preferred embodiments a predetermined quantity of a pharmaceutical or medical composition comprising a fluid or a solid such as a powder or a lyophilized agent is contained in, or produced in an ampoule or blister dosage form that is crushed by a plunger with sufficient force to drive the dosage form against a piercing mechanism, piercing the dosage form and forcing the liquid or solid contents from the dosage form and through a delivery channel or channels into a spray to be directed to the recipient. A predetermined quantity refers, in most instances, to a single dose of medication or a pharmaceutical, biologic or medical composition, and in certain embodiments to a prescribed dose. A predetermined quantity of fluid or solid dose may also be a partial dose when delivery of a dose is administered in two or more spray events.

Any pharmaceutical agent or diagnostic reagent that is deliverable in a powder, lyophilized, or liquid form is contemplated in the present disclosure, including but not limited to antibiotics, antipyretics, anti-inflammatories, biologics, vitamins, co-factors, enzymes, inhibitors, activators, nutrients, vaccines including DNA based killed or live virus or microorganisms, nucleic acids, proteins, peptides, antibodies, peptide mimetics, aptamers or other agents or pharmaceutical compositions known in the art. The pharmaceutical compositions are in the form of a liquid, a powder, a lyophilized agent, or any combination thereof, and include one or more active agents, which may be combined or mixed with pharmaceutically acceptable carriers, solvents, diluents, preservatives, surfactants, salts, adjuvants, viscosity agents, buffers, chelators, or other ingredients known to those in the art as needed.

In preferred embodiments when the dosages are intended to be delivered or administered to a human subject, the preferred agents, e.g., matrix materials, therapeutic agent, active agent, surfactant, and functional excipients of the present disclosure are pharmaceutically acceptable materials. As used herein, "pharmaceutically acceptable carrier" or "pharmaceutically acceptable materials" includes any and all solvents, dispersion media, coatings, antibacterial and antifungal agents, isotonic and absorption delaying agents, absorption enhancing agents and the like. The use of such media and agents for pharmaceutically active agents is well known in the art. Except insofar as any conventional media or agent is incompatible with the active agent, its use in the therapeutic compositions is contemplated. Supplementary active agents can also be incorporated into the compositions. The phrase "pharmaceutically acceptable" also refers to molecular entities and compositions that do not produce an allergic or similar untoward reaction when administered to a human or animal.

The present disclosure arose in part from the observations that regulating the velocity of a singulated high velocity stream of laminar flow liquid directed at a deposition target from a crushable blister through an internal piercing mechanism will reduce rebound of the dispensed liquid from the targeted deposition site improving the net delivered dose volume. High velocity and singularity of the laminar stream also imparts a general discomfort experienced by the user.

The present invention can be described in certain embodiments as a piercing device for delivering a predetermined quantity of liquid or powder contained in a crushable blister into a spray or mist. The device is preferable contained in a dome or modified dome shaped blister as an internal piercing mechanism such that, when the blister is crushed by a ram or plunger, for example the internal piercing mechanism is forced against the sealed side of the blister and penetrates the seal via a central lancet tip and the contents of the blister are forced out through the piercing device in a spray pattern. As used herein a modified dome is indicative of a basic hemispherical shape formed by pushing or drawing a stretchable material through a round opening in a die, and in which the formed material has been altered by the shape of a plunger to provide a radial or other shaped projection, depression or other configuration at the top of the hemisphere for close fit of a piercing device, for example, or to have an altered slope of the sides. Any such configurations are contemplated by the present disclosure.

The configuration of preferred embodiments can be better understood by referring to the drawings, where it can be seen that the piercing device includes a lancet tip for piercing a film and that the tip is of smaller diameter than the central projection and can be described as a generally sharp feature comprising 2 or more sides for the purpose of piercing a piercable material.

In certain embodiments the piercing device can include structural features on the surface of the internal delivery channel to affect the spray pattern and droplet size of a fluid or powder forced through the piercing device during use. The structural features are designed to be compatible with the particular medicament or agent to be delivered and vary depending on the viscosity, delivery site and other factors specific to the particular medicament. As such the structures can include, but are not limited to angular wall and top boundaries of the internal structures, or steps, flutes, ribs, or a combination thereof. In addition to the internal structures, the delivery channel can include bends and turns to produce turbulence in a fluid as it travels through the delivery path. Such bends can be right angles, or 90° turns, or they can be angles from about 20° to about 135°. The fluid paths in the base can also be arranged to produce a vortex in the fluid or powder as it is forced through the delivery channel.

In certain embodiments the delivery channel terminates in one or more openings for dispensing the contents of a blister to the intended target. In certain embodiments, the inventors have discovered that a plurality of openings arranged around a central piercing lancet offers certain advantages over a single center bore. For example, the spray from centerline bore/outlet nozzles is prone to deflection by blister foil flap-type tearing. Lancet tip piercers with radial outlets tear the blister foil along three axes which radiate from a central point of initial puncture, allow the outlets to quickly and completely clear the foil, thus avoiding deflection of the spray pattern. The inventors have observed in the described devices that spray deflection from central bore piercers can exceed 45 degrees, whereas spray deflection from lancet-tip radial outlet piercers does not exceed ten degrees, and rarely exceeds five degrees.

Additionally, the inventors have discovered that the spray velocity of central bore piercers, which can lack the means to introduce significant turbulence into the stream, is much greater than the velocity from piercers with multiple outlets which require the internal flow to collide with and be redirected by non-linear channels. For example, blisters filled to 25 uL of water and fitted with central bore piercers generate spray velocities in excess of 100 feet per second for more than 50% of their spray lifetimes, whereas blisters filled to 25 ul of water and fitted with lancet-tip radial-outlet piercers generate velocities below 60 fps throughout their entire lifetimes. Furthermore, the cross-sectional area of a fluid stream as it contacts the surface of the eye (at a range of approximately 1 inch) is approximately the same as the cross sectional area of a central bore. That is, central bore piercers having a 500 μm diameter outlet generate streams whose cross-sectional diameter is approximately 500 μm. In a circle of multiple radial outlet piercers, whose outlets are arranged within a circle of diameter 2-3 mm the generated will be similar diameter. Therefore, given a blister filled with 25 uL of water, the significantly greater velocity and significantly narrower stream diameter of a central bore piercer results in a spray which (at a range of approximately 1 inch) rebounds from the surface of the average human eye. While the same delivered dose from a lancet-tip radial outlet piercer delivered at lower velocity and greater area stays on the eye, captured by the eye's tear film In certain preferred embodiments the disclosure is a dosage from containing a piercing device as described herein. The dosage form can be a crushable blister or ampoule containing a liquid or powder medical composition. Such dosage forms are known for use in delivery systems in which a ram or piston is forced against the dosage form, forcing the contents out through a delivery channel or channels.

The disclosure can also be described in certain embodiments as an internally pierced dosage form including a substantially dome shaped, or modified dome shaped flexible blister; a substantially round pierceable surface sealed to the base of the dome-shaped blister; and an internal chamber; wherein the internal chamber contains a piercing device and a fluid composition and wherein the piercing device comprises: a base; a substantially hollow, elongated member extending from the base forming a shoulder region opposite the base end of the elongated member; an internal delivery channel extending from the base to the tip and formed by the hollow interior of the elongated member; an elongate member projecting from the shoulder region of the elongated member wherein the circumference of the elongate member is less than the circumference of the shoulder region and ending in a piercing tip opposite the shoulder end wherein the tip is configured to form a lancet type tip; and further forming a discharge port in fluid communication with the internal delivery channel or channels; and one or more inlet openings on the base end and one or more conduits providing fluid communication between the one or more inlet ports and the internal channel to allow fluid communication to one or more outlets resulting in a disrupted, via turbulence, spray or mist.

The dosage form can also be described wherein the piercing device further includes structural features on the surface of the internal delivery channel to affect the spray pattern and droplet size of a fluid forced through the piercing device during use, including but not limited to steps, flutes, ribs, or a combination thereof. The internal channel can also provide one or more bends or turns to impart turbulence or a vortex to the fluid during delivery.

In certain embodiments, therefore, the disclosure may also be described as a piercing nozzle for dispensing a fluid or solid composition from a dosage form with a particular volume, in a controlled spray pattern and droplet size. The nozzle includes an elongate member with an inlet end and a discharge end, an internal channel connecting the inlet end and the discharge end in fluid communication, one or more inlet openings in the inlet end, a lancet shaped tip in proximity to a discharge opening in the discharge end, and features on the internal chamber surface to control the spray pattern and droplet size of a fluid forced through the nozzle (s). The inlet ports are designed to provide a fluid path into the internal channel that includes one or more angled turns. The inlet ports can also be designed to produce a vortex or turbulence in the liquid or solid composition as it is forced through the ports. Features in the internal channel can also include, but are not limited to, steps, flutes, ribs, constrictions, contours, and related structures to produce the desired droplet size and spray geometry. In certain embodiments, the piercing tip may be on the discharge end of the elongated member, or on the inlet end. The piercing nozzle can be contained in a dosage form. The disclosure includes, therefore, a dosage form that comprises the piercing nozzle and a pharmaceutical composition.

In certain embodiments the present disclosure can be described as an internally pierced dosage form that includes a substantially dome shaped, flexible blister, a substantially round pierceable surface sealed to the base of the dome-shaped blister, and an internal chamber containing a piercing nozzle as described herein and a liquid composition. In certain embodiments the piercing nozzle includes a base and a piercing end, and wherein the base is attached to the modified dome shaped blister and the piercing end is proximate the pierceable surface and wherein the piercer has a lancet shaped piercing tip.

It is contemplated that any embodiment discussed in this specification can be implemented with respect to any process, device, or composition of the invention, and vice versa. The term "about" as used herein is defined as being "close to" or "approximately" as understood by one of ordinary skill in the art, and in one non-limiting embodiment the terms are defined to be within experimental error, or within 10%, within 5%, within 1%, or within 0.5%. The term "substantially" and its variations as used herein are defined as being largely but not necessarily wholly what is specified as understood by one of ordinary skill in the art, and in one non-limiting embodiment substantially refers to ranges within 10%, within 5%, within 1%, or within 0.5%. The use of the word "a" or "an" when used in conjunction with the term "comprising" in the claims and/or the specification may mean "one," but it is also consistent with the meaning of "one or more," "at least one," and "one or more than one."

It is to be understood that each of the variously stated ranges herein is intended to be continuous so as to include each numerical parameter between the stated minimum and maximum value of each range. It is to be further understood that, while not intending to limit the applicability of the doctrine of equivalents to the scope of the claims, each numerical parameter should at least be construed in a manner consistent with the reported number of significant digits for each numerical parameter and by applying ordinary rounding techniques. It is to be even further understood that, while not intending to limit the applicability of the doctrine of equivalents to the scope of the claims, even though a number may be contained within a numerical range wherein at least one of the minimum and maximum numbers of the range is preceded by the word "about," each numerical value contained within the range may or may not be preceded by the word "about." For Example, a range of about 1 to about 4 includes about 1, 1, about 2, 2, about 3, 3, about 4, and 4.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used in this example and throughout the specification, unless the context indicates otherwise, these terms are defined as follows.

First fissure: The primary and immediate initial split in the lidstock material that precedes the actual puncture.

Distal end: On any extremity, the furthest point from the proximal end, i.e. for the piercing mechanism, the point furthest from the piercer base.

The Drape: During puncture, the lidstock material that is in between the piercer tip and the main body of lidstock material.

Non-contact Drape: That portion of the drape that does not contact the piercer.

Bilobal or having a bilobal cross-section is meant to convey a bean or kidney shaped cross-section having 2 lobal shapes joined in a center section as illustrated in the attached Figures.

In certain embodiments the unit dosage forms of the present disclosure are blisters that can be manufactured as described in US Application Publication No. 20090071108, incorporated in its entirety herein by reference. The manufacturing processes for shaping articles for unit-dose packaging with at least one formed recess (e.g., a blister), in particular for unit-dose packaging of pharmaceutical dosage forms, can include a step of drawing the film material (e.g., metal-plastic foil) with one or more plungers to form a primary contour, the contour having a depth of at least 100% and up to 150% of the depth of the final formed recess. A second stage involves shaping the primary contour with one or more plunger(s) to the desired final formed recess, with a depth that is less than the depth of the primary contour, while substantially maintaining the surface area of the primary contour formed in the first stage. The formed recess may be formed using warm-forming or cold-forming techniques.

The disclosed devices may be described in certain embodiments as devices for dispensing a predetermined quantity of fluid into the nasal passage of a user, or into the eye or ear of a user, in which the predetermined quantity of fluid is contained in, or produced in an ampoule or blister dosage form that is crushed by a plunger with sufficient force to drive the dosage form against a piercing mechanism, piercing the dosage form and forcing the liquid contents from the dosage form and through a delivery channel into a spray to be directed to the user. A predetermined quantity refers, in most instances to a single dose of medication or a pharmaceutical or medical composition, and in certain embodiments to a prescribed dose. A predetermined quantity of fluid may also be a partial dose when delivery of a dose is administered in two or more spray events. Any pharmaceutical agent that is deliverable in a powder or liquid form is contemplated in the present disclosure, including but not limited to antibiotics, antipyretics, anti-inflammatories, biologics, vitamins, co-factors, enzymes, inhibitors, activators, nutrients, aptamers, thioaptamers, vaccines including killed or live virus or microorganisms, nucleic acids, proteins, peptides, antibodies, peptide mimetics, or other agents known in the art. The medical compositions are in the form of a liquid, a powder, or a combination of liquid and powder and include one or more active agents and combinations of pharmaceutically acceptable carriers, solvents, diluents, preservatives, surfactants, salts, adjuvants, viscosity agents, buffers, chelators, or other ingredients known to those in the art as needed.

The volume of droplets or particles dispensed from the devices will depend on the site of dispensing as well as the content and viscosity of the medication to be delivered. In certain embodiments droplet to be delivered to the eye would be from 1 µl to 50 µl, or more typically from 7 µl to 50 µl. Dosage for nasal administration are typically from 75 µl to 500 µl and dosages for oral or topical cutaneous administration can be larger, as much as 1000 µl or more. The volume and size of droplets or particles released by a device can be adjusted to maximize the therapeutic benefit of the dispersed substance. The volume of substance dispensed depends on the size of the compartment containing the substance, the unit dosage form blister, the piercer, the fill level, the degree to which the dosage form is compressed by the device and other variables in the construction of the devices, as well as characteristics of the substance dispersed, which are well understood by those skilled in the art. These variables can be appropriately dimensioned to achieve dispersal of a desired volume or droplet size of liquid or particle size of substance to the user. One of skill in the art understands that residual liquid or other substance after dispersal is taken into account when formulating the appropriate parameters for dispersing the desired dosage volume.

An advantage of the devices and unit dosage form designs set forth herein is that the sterility of the administered substance is maintained until the moment of use. Maintaining sterility until the moment of use minimizes or eliminates the need to use preservatives or bacteriostatic compounds in the substances administered, without risking contamination. In addition, if the unit dosage form is damaged, or is otherwise defective, the devices do not administer the substance, which may no longer be sterile. For example, if an unit dosage form is defective in the area of the pierceable section, or develops a leak, the devices will not dispense the substance properly because sufficient pressure will not be generated in the unit dosage form to effectively release the substance.

The dosage forms of the disclosure are described, in certain embodiments as including a dispensing blister chamber that contain a piercing device, wherein the piercing device is a substantially hollow, elongate member with a base end and a piercing tip opposite the base end and providing a discharge nozzle. In certain embodiments the dispensing blister conforms to at least the base end of the piercing device effective to support and hold the piercing device in place during manufacture and use of the dosage form. The piercing devices include one or more inlet openings on or near the base end and an internal conduit providing fluid communication between the one or more inlet ports and the discharge nozzle; and the surface of the internal conduit comprises structural features such as contours, steps, flutes, ribs, constrictions, or a combination thereof to control the spray pattern and droplet size of a fluid forced through the piercing device. It is a further aspect of the disclosure that the inlet openings provide a fluid path from the interior of the dispensing blister chamber into the internal conduit that comprises one or more bends, and that the combination of angular turns and the structural features of the internal conduit create vortices in the fluid as it is forced through the piercing mechanism.

The structural features can be designed, for example, for different types of spiral, vertical and other flow and the design can be adjusted for different viscosities of the fluid or solid to be dispensed. For example, structural features may be added to create a vortex, to further mix the contents of the blister, to change the fluid property type from laminar to turbulent or vice versa or to change fluid properties such as pressure, velocity, surface tension or viscosity and can also aid in reconstitution of lyophilized or powdered agents. Additionally, the inlets into the internal conduit can include bends of angles from about 1° to 90°, or more in combinations in order to create the desired spray plume geometry for a particular medicament or liquid dose.

In certain embodiments, a shaped blister dosage form as described herein that contains medication and an internal piercing nozzle, is configured for use in a smaller diameter dispensing mechanism, while still providing an accurate dose of medicine in the form of a controlled spray. A blister strip including a plurality of such dosage forms can include a blister material layer in which the dosage forms are formed, and a lid material bonded to the blister material. A concentric sealing area provides a resilient seal that is not broken when the dosage forms are crushed to deliver the contained medication.

To produce a controlled spray of liquid when bursting a sealed formed recess, such as a shaped blister, an internal piercer inside the sealed blister may be used, and may be positioned such that it maintains contact with the lid material. The internal piercer can be constructed of any suitable materials such as ceramic, glass, metal, thermoplastics, including but not limited to PET, polypropylene, polyethylene, or PEEK, Ultem, PrimoSpire and other pharmaceutical grade FDA approved materials of sufficient hardness to penetrate the lid material. The second, subsequent and/or final plunger(s) may be designed to shape the formed recess such that the internal piercer is held in place within the formed recess, e.g., through manufacture, handling, transportation, storage, and actual use. For example, in a shaped blister, a protruding structure, an indentation, a diaphragm or an annulus is formed to conform to the shape of the base of the internal piercer. The protruding structure, indentation, diaphragm, or annulus provides support for and holds the internal piercer in place during assembly and during dispensing. Thus, these structures function to capture the internal piercer (e.g., restrict vertical movement of the piercer), thereby holding it in place. The internal piercer may also be held in place through manufacture and actual use by, for example, press fit, welding, hydrostatic forces, or electrostatic forces. The shaped blister can also be formed by the second or subsequent plunger such that it insures that the protruding structure, indentation, diaphragm, or annulus seals to the internal piercer in order to achieve the desired spray pattern.

In preferred embodiments, the internal piercer includes one or more hollow tubes or channels (the delivery channel) through which the pharmaceutical dosage flows as the shaped recess is compressed and pierced. The tip of the piercer can be in the shape of a nipple, a pyramid, or a projection from the main body in order to reduce the formation of a puncture flap in the lid material after puncture. The inside diameter of the piercer outlet(s) can range from about 0.010 inches to about 0.05 inches, but in certain preferred embodiments is about 0.025 inches. The internal diameter, shape, or surface texture of the delivery channel, whether in, near, and/or at the exit point, may contain a nozzle or may be varied to form the optimum droplet size and spray plume geometry of the pharmaceutical dosage form as it exits the shaped article, as well as control the velocity, pressure, pattern, distribution, and aim of the released substance. Thus, the nozzle system and the piercer may be integrated into a single unit. The nozzle system can also be designed to determine the mixing of the substance as it is released.

To successfully dispense the medication, the medication must flow through the piercing nozzle with the correct magnitude and vectors of velocity to create the desired spray geometry. As described herein, this is accomplished by pressing on the blister form with sufficient force to push the piercing nozzle through the lid material, completely crushing the dosage form and forcing the contents through the nozzle with the required velocity. During this dispensing operation, the seal of the lid material to the blister material must be strong enough that no leakage occurs prior to the nozzle piercing the lid. The smaller size required by certain dosage situations, such as intranasal administration present greater challenges to the seal of the lid material to the blister material.

In certain embodiments the piercing mechanism is contained in the dosage form with the fluid to be delivered. Such internal piercing mechanisms can include an internal chamber, one or more inlet openings arranged to force one or more bends or changes in direction as the fluid flows into the internal chamber, a discharge outlet or outlets, and features on the internal surface to control the spray pattern and droplet size of a fluid forced to flow through the nozzle(s). The changes in direction can be of any appropriate angle, including from about 1° to about 90° or more. The design of such features is known to those of skill and include steps, flutes, ribs, or a combination thereof.

In certain embodiments the disclosure may be described as a piercing nozzle for dispensing fluid from a dosage form in a controlled spray pattern and droplet size. The nozzle includes a substantially elongate member with an inlet end and a lancet tip on the discharge end, an internal channel connecting the inlet end and the discharge end in fluid communication, one or more inlet openings in the inlet end, one or more discharge openings in the discharge end, and features on the internal chamber surface to control the spray pattern and droplet size of a fluid forced through the nozzle. The inlet ports are designed to provide a fluid path into the internal channel that includes one or more right angle turns. The inlet ports can also be designed to produce a turbulence or vortex in the liquid as it is forced through the ports. Features in the internal channel can also include, but are not limited to steps, flutes, ribs, and related structures to produce the desired droplet size and spray geometry. In certain embodiments, the piercing tip may be on the discharge end of the elongated member, or on the inlet end. The piercing nozzle can be contained in a dosage form. The disclosure includes, therefore, a dosage form containing the piercing nozzle and a medical or pharmaceutical composition.

In certain embodiments the present disclosure can be described as an internally pierced dosage form that includes a substantially modified dome shaped, flexible blister, a substantially round pierceable surface sealed to the base of the modified dome-shaped blister, and an internal chamber containing a piercing nozzle as described herein and a liquid composition. In certain embodiments the piercing nozzle includes a base and a piercing end, and wherein the base is attached to the modified dome shaped blister and the piercing end is proximate the piercable surface.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 is a side view of an embodiment of a lancet tipped piercer.

FIG. 2 is a side view of the piercer shown in FIG. 1 rotated 120° about the center of the lancet.

FIG. 3 is a perspective top view of the piercer shown in FIG. 1.

FIG. 4 is top plan view of the piercer shown in FIG. 1.

FIG. 5 is a bottom plan view of the bottom of the base top of the piercer shown in FIG. 1.

FIG. 6 is a sectional view of a piercer as shown in FIG. 1.

FIG. 7 is an alternate sectional view of a piercer as shown in FIG. 1.

FIG. 8 is a sectional view through the body of the piercer as shown in FIG. 1.

FIG. 9 is a sectional view through the piercing region of a piercer as shown in FIG. 1.

FIG. 10 is a horizontal section view through a base of a piercer as shown in FIG. 1.

DETAILED DESCRIPTION

Preferred embodiments of the present disclosure are directed to dosage forms that contain a measured dose of one or more pharmaceutically active agents and a piercable section such that the dosage form can be pierced to release the contents under pressure. When using the term "under pressure" in the disclosure, it is understood that the pressure is typically an externally applied pressure rather than internal pressure within the dosage form itself. In typical operation, a plunger, lever, ram, wheel, or some other mechanical device contacts the dosage form with sufficient force to crush the dosage form against a piercing member and force the contents out of the opening. The dosage form can be generated using methods well known to those of skill in the art, including, for example, form fill seal technology or blow fill seal technology, or by deep draw forming as described in U.S. Application Publication No. 2009/0071108, incorporated herein in its entirety by reference.

The form-fill-seal process can be used to create a blister, for example a blister pack, from rolls of flat sheet or film, inserted with a piercing mechanism, filled with the pharmaceutically active agent, and closed or sealed on the same equipment. This process involves a formed base which has the cavity in which the pharmaceutically active agent, or an agent that may be mixed or combined with a pharmaceutically active agent, is placed, and a lidding, for example of foil, through which the agent is dispensed out of the blister. Blow fill seal technology involves forming, filling, and sealing a dosage form in a continuous process in a sterile enclosed area inside a machine.

The film layer may include a variety of different materials, including, but not limited to, thermoplastics, polymers, copolymers, composites and laminates. When the unit dose is a pharmaceutical dosage form, the film will need to be able to undergo aseptic manufacturing processes to produce sterile shaped articles, for example gamma ray irradiation. Preferably the film is flexible but capable of holding its shape, can be crushed with minimal force, creates a barrier, withstands radiation, and has desirable chemical properties (e.g., does not react with the pharmaceutical dosage form to be administered). For blister packs, the film is preferably a foil laminate, and more preferably a metal-plastic laminate. The metal-plastic laminate comprises a metal foil coated on at least one side, or on both sides, with a plastic layer. If the metal-plastic laminate comprises a plastic layer on both sides of the metal foil, the plastic layers may be the same type of plastic layer, or different types of plastic layers.

Materials which may be used in the plastic layer of the laminate are well known by those skilled in the art and include, but are not limited to, a variety of commercially available polymers and copolymers, such as polyvinylchloride, nylon, nylon derivatives, polybutylene terephthalate, polyethylene terephthalate, polyethylene, polypropylene, polystyrene, polyacetal, vinylidene chloride, propylene ethylene copolymers, polyethylene napthalate, fluoropolymers, cyclic polyolefins, polyamides, and similar materials or combinations thereof. The plastic layer may be present in the laminate at a thickness of about 8 μm to about 80 μm, about 10 μm to about 70 μm, about 15 μm to about 60 μm, about 20 μm to about 50 μm, or about 25 μm to about 40 μm, and any ranges therein. The plastic components may be non-stretched, or alternatively uniaxially or biaxially stretched, or may be thermoplastics such as halogen-containing polymers, polyolefins, polyamides, polyesters, acrylonitrile copolymers, or polyvinylchlorides. Typical examples of thermoplastics of the polyolefin type are polyethylenes such as low density polyethylene (LDPE), medium density polyethylene (MDPE), high density polyethylene (HDPE), uniaxially, or biaxially stretched polypropylenes, polypropylenes such as cast polypropylene and uniaxially or biaxially stretched polyethylene terephthalate (PET) from the polyester series. The above examples are in no way meant to be limiting, as other materials known in the art may be used in the plastic layer as well.

Examples of plastics based on halogen-containing polymers include but are not limited to polymers of vinylchloride (PVC) and vinyl plastics, containing vinylchloride units in their structure, such as copolymers of vinylchloride and vinylesters of aliphatic acids, copolymers of vinylchloride and esters of acrylic or methacrylic acids or acrylonitrile, copolymers of diene compounds and unsaturated dicarboxyl acids or their anhydrides, copolymers of vinylchloride and vinylchloride with unsaturated aldehydes, ketones, etc., or polymers and copolymers of vinylidenchloride with vinylchloride or other polymerizable compounds. The vinyl-based thermoplastics may also be made soft or pliable in a conventional manner by means of primary or secondary softeners.

If the plastic films comprise polyesters (PET-films), examples of polyesters include but are not limited to polyalkylene-terephthalate or polyalkylene-isophthalate with alkylene groups or radicals with 2 to 10 carbon atoms or alkylene groups with 2 to 10 carbon atoms interrupted by at least one oxygen atom, such as, e.g., polyethylene-terephthalate, polypropylene-terephthalate, polybutylene-terephthalate (polytetramethylene-terephthalate), polydecamethylene-terephthalate, poly 1,4-cyclohexyldimethylol-terephthalate or polyethylene-2,6-naphthalene-dicarboxylate or mixed polymers of polyalkylene-terephthalate and polyalkylene-isophthalate, where the fraction of isophthalate amount, e.g., to 1 to 10 mol. %, mixed polymers and terpolymers, also block polymers and grafted modifications of the above mentioned materials. Other useful polyesters are known in the field by the abbreviation PEN. Other polyesters are copolymers of terephthalic acid, a polycarboxyl acid with at least one glycol, copolymers of terephthalic acid, ethyleneglycol and an additional glycol, polyalkylene-terephthalates with alkylene groups or radicals with 2 to 10 carbon atoms, polyalkylene-terephthalates with alkylene groups or radicals with 2 to 10 carbon atoms which are interrupted by one or two oxygen atoms, polyalkylene-terephthalates with alkylene groups or radicals with 2 to 4 carbon atoms, and polyethyleneterephthalates (e.g., A-PET, PETP, PETG, G-PET). Glycol-modified polyesters are also referred to as PETG.

Examples of polyolefins for plastic films include but are not limited to polyethylenes (PE), e.g., high density polyethylene (HDPE, density larger than 0.944 g/cm), medium density polyethylene (MDPE, density 0.926-0.940 g/cm), linear polyethylene of medium density (LMDPE, density 0.926.0.940 g/cm), low density polyethylene (LDPE, density 0.910-0.925 g/cm), and linear low density polyethylene (LLDPE, density 0.916-0.925 g/cm), for example as non oriented (PE film) or uniaxially or biaxially oriented films (oPE film), polypropylenes (PP), such as axially or biaxially oriented polypropylene (oPP film), or cast polypropylene (cPP film), amorphous or crystalline polypropylene or mixtures thereof, ataktic or isotaktic polypropylene or mixtures thereof, poly-1-butene, poly-3-methylbutene, poly-4-methylpententene and copolymers thereof, polyethylene with vinylacetate, vinylalcohol, acrylic acid, such as, e.g., ionomeric resins, such as copolymers of ethylene with 11% acrylic acid, methacrylic acid, acrylic esters, tetrafluorethylene or polypropylene, statistical copolymers, block polymers or olefin polymer-elastomer mixtures, ionomers, and ethylene-acrylic acid copolymers (EAA).

If the plastic films comprise polyamide films (PA), examples of polyamides include but are not limited to polyamide 6, a homo-polymer of [ε]-caprolactam (polycaprolactam); polyamide 11, polyamide 12, a homo-polymer of [o]-laurinlactam (polylaurinlactam); polyamide 6,6, a homo-polycondensate of hexamethylenediamine and adipinic acid (polyhexa-methylene-adi-amide); polyamide 6,10, a homo-polycondensate of hexa-methylene-diamine and sebacinic acid (poly-hexa-methylene-sebacamide); polyamide 6,12, a homo-polycondensate of hexa-methylene-diamine and dodecandic acid (poly-hexa-methylene-dodecanamide) or polyamide 6-3-T, a homo-polycondensate of trimethyl-hexa-methylene-diamine and terephthalic acid (poly-trimethyl-hexa-methylene-terephthalic-amide), and mixtures thereof.

If the plastic comprise acrylnitrile-copolymers, examples of acrylnitrile-copolymers include but are not limited to copolymers of acrylonitrile or methacrylnitrile with acrylic acid esters, vinyl-carboxylate esters, vinyl halides, aromatic vinyl compounds or unsaturated carboxylic acid and diene, and acrylnitrile-methylacrylate copolymers.

Metals which may be useful in the foil component of the laminate are those that can be formed into a foil with the physical and chemical properties (e.g., thickness, malleability, temperature resistance and chemical compatibility) sufficient to adhere to the plastic layer(s) and remain intact during the forming processes disclosed herein. Such metals include, but are not limited to, aluminum, iron, nickel, tin, bronze, brass, gold, silver, chrome, zinc, titanium, and copper, combinations thereof, as well as alloys including the aforementioned metals, such as steel and stainless steel. The metal foil may be present in the laminate, for example, at a thickness of about 8 μm to about 200 μm, about 10 μm to about 150 μm, about 15 μM to about 125 μm, about 20 μm to about 100 μm, or about 25 μm to about 80 μM, and any ranges therein. In certain embodiments the foils, e.g., aluminum foil, may have a purity of at least about 98.0%, more preferably at least about 98.3%, still more preferably at least about 98.5%, and most particularly at least about 98.6%. Aluminum foils of the aluminum-iron-silicon or aluminum-iron-silicon-manganese types may also be used. Other suitable metal foils known in the art may be used as well.

The laminate may also include one or more adhesive layers between the foil layer and the plastic layer. The same or different adhesives may be used to adhere the plastic to the metal foil on each side. The adhesive layer should be capable of forming a bond with the plastic layer and the foil layer, and generally should be of a thickness of between about 0.1 μm and about 12 μm, more typically between about 2 μm and about 8 μm, and any ranges therein. Any number of adhesives known in the art may be used, and the adhesives may be applied using a number of known techniques. Suitable adhesives may contain one or more solvents, be solvent-free, or may be acrylic adhesives or polyurethane adhesives. The adhesive may also be a thermal bonding adhesive, for example an ethylene-vinylacetate copolymer or a polyester resin. The adhesive may also be of a type which hardens upon exposure to electromagnetic rays, for example ultraviolet rays. The laminate may also be formed by hot calendaring, extrusion coating, co-extrusion coating or through a combination of processes. Example adhesives that may be used in the present disclosure include but are not limited to polyethylene (PE) homopolymers, such as LDPE, MDPE, LLDPE, and HDPE; PE copolymers, such as ethylene-acrylic acid copolymers (EAA), ethylene methacrylic acid copolymer (EMAA); polypropylene (PP); PP copolymers; ionomers; and maleic anhydride grafted polymers.

In another embodiment, the film, e.g., a metal-plastic laminate, may feature a sealing layer in the form of a sealable film or a sealable counting on one of the outer lying sides, or on both of the outer sides. The sealing layer will be the outermost layer in the laminate. In particular, the sealing layer may be on one outer side of the film, which is directed towards the contents of the shaped packaging, in order to enable the lid foil or the like to be sealed into place.

Another embodiment for forming blister packaging is a laminate of aluminum, where the metal foil is coated with a plastic on each side. Aluminum foil is known to provide superior barrier properties to protect the contents of the package. The plastic coating provides an effective means of sealing the package plus provides a protective coating for the aluminum, and may also provide the ability to print on the package.

In some embodiments, the thicknesses and compositions of the laminate include but are not limited to:
i. OPA/ALU/PE (12 μm/60 μm/30 g/m$^2$);
ii. OPA/ALU/PE (12 μm/45 μm/30 g/m$^2$);
iii. OPA/ALU/PVC (12 μm/60 μm/30 g/m$^2$);
iv. OPA/ALU/PVC (12 μm/45 μm/30 g/m$^2$);
v. OPA/ALU/PP (12 μm/60 μm/30 g/m$^2$); and
vi. OPA/ALU/PP (12 μm/45 μm/30 g/m$^2$). As used above, OPA stands for oriented polyamide, ALU stands for aluminum, PE stands for polyethylene, PVC stands for polyvinylchloride, and PP stands for polypropylene.

An embodiment of a turbulating piercer is shown in FIG. 1. As used herein the term turbulating piercer is meant to convey its ordinary meaning in the art, and is used to indicate that the piercer, during use, i.e. during delivery of a fluid that enters the inlet opening under pressure, creates a laminar flow as the fluid flows through the radial inlet channel and creates a turbulent flow as the fluid flows into and through the internal cavity and outlet channels or cannulae, such that the fluid is released through the outlet openings as a spray or mist rather than a stream.

As shown in the FIG. 1, the piercer 10 includes a base 12, which is a circular base in the embodiments shown, and an elongated trilaterally symmetrical member 14 projected from and concentric with the center of the base 12. It is understood that the base can be provided in alternate geometrical shapes for various applications, including but not limited to oval or polygonal, for example. The projected member 14, which can also be called the piercer body or the projection can be attached to, contiguous with, or integrally formed with the base. The piercer including the base and the projection can be a single piece and configured to be held within the interior of a closed, fluid containing cavity such as the interior of a formed recess or a blister as described elsewhere herein. In particular, the piercer is configured to be used in a formed blister and delivered under pressure in devices as described in commonly owned U.S. Pat. Nos. 7,669,597, 7,963,089, 8,047,204, 8,272,194, 8,377,009, and U.S. application Ser. Nos. 13/770,861, 13/625,614, 13/233,661, 13/191,315, 13/149,584, and 12/851,524, each of which is incorporated herein by reference in its entirety.

Figure 3:
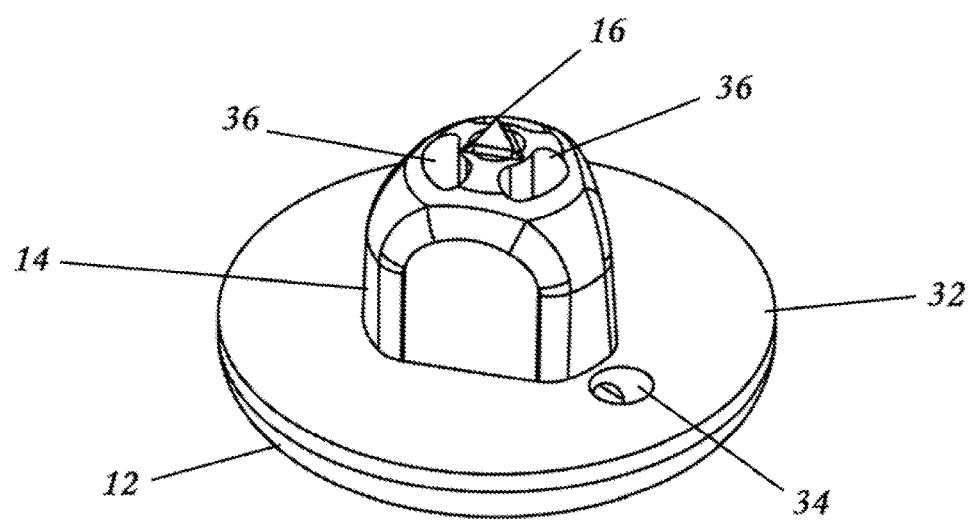
Figure 4:
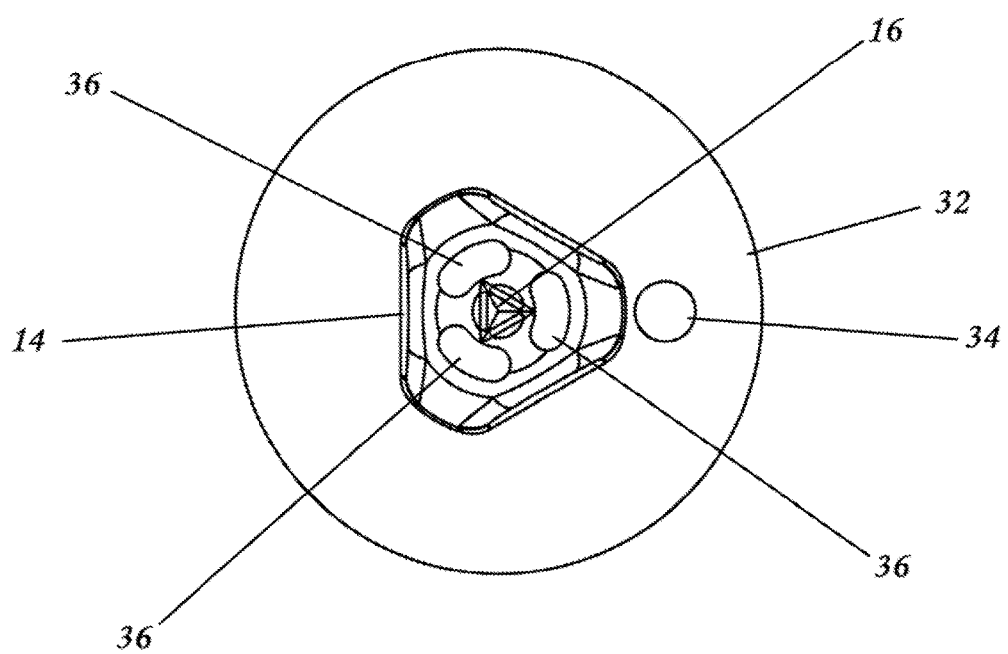
Figure 7:
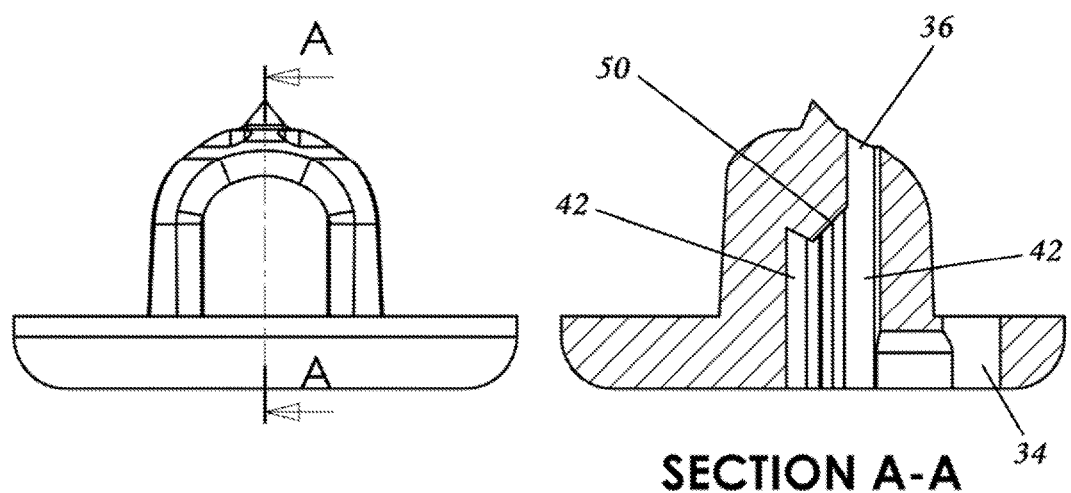
Figure 8:
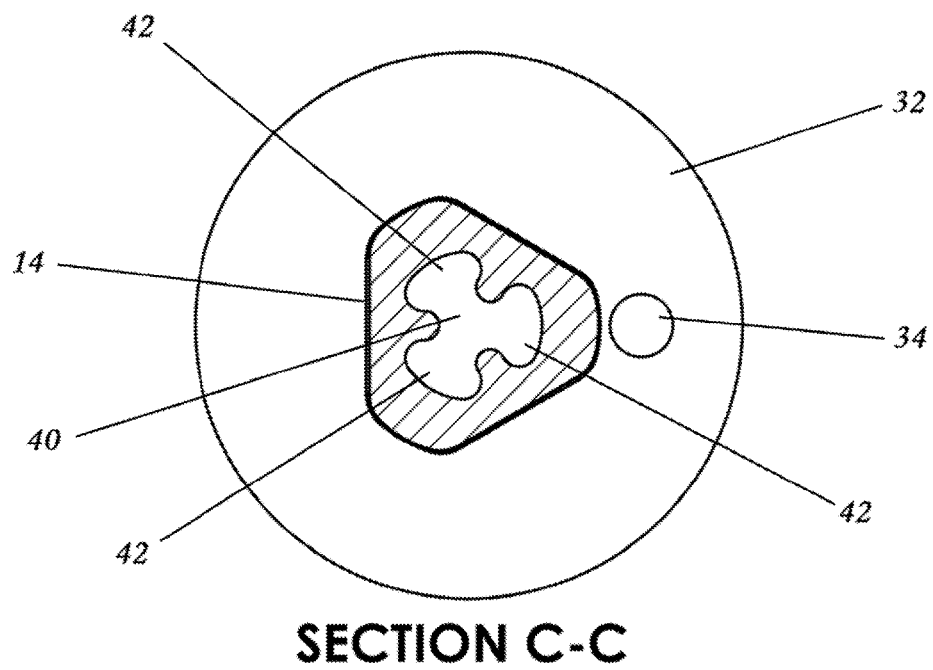
Figure 8:
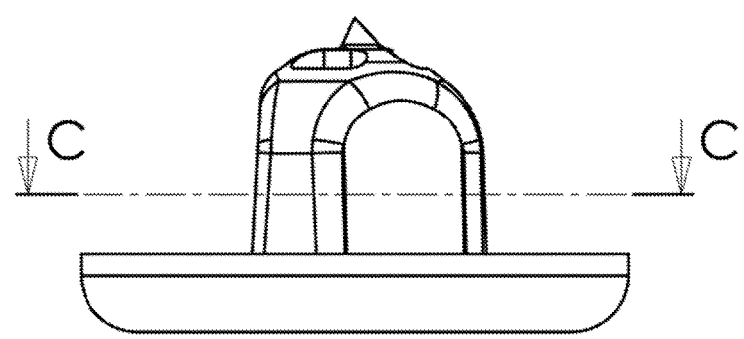
Figure 9:
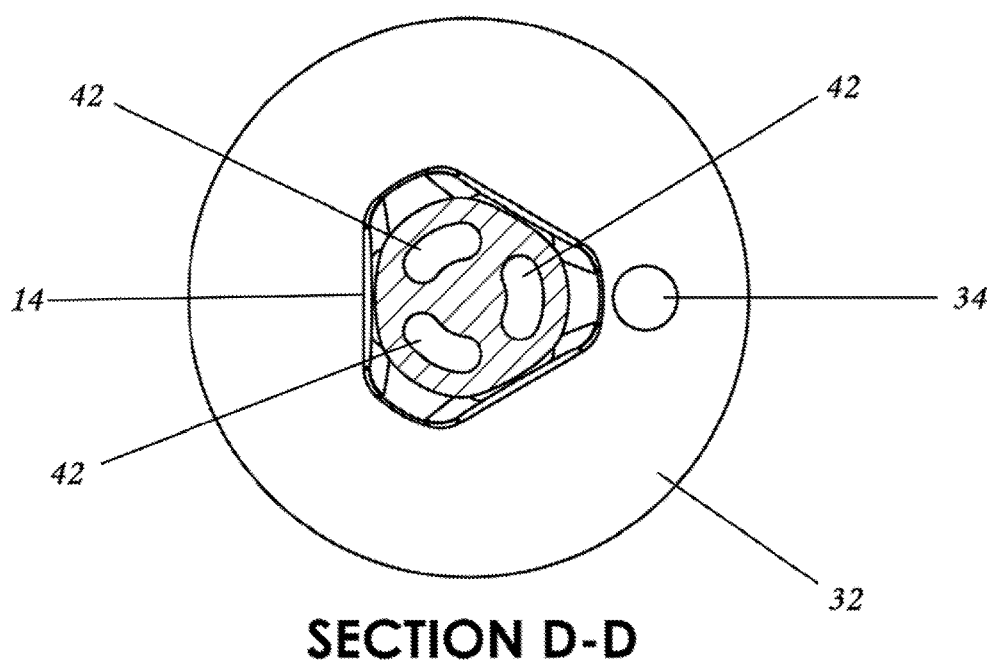
Figure 9:
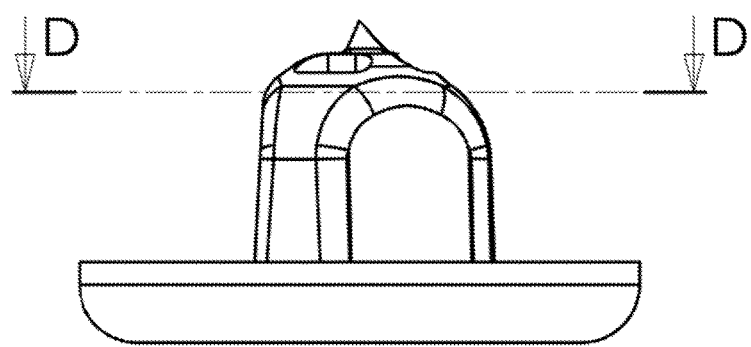

As shown in FIG. 3, the top 32 of the base provides a single inlet 34 to the internal flow path of the piercer and the projection provides one or more outlets or discharge ports 36 near the lancet for the release of the fluid contents of the blister. As seen in FIG. 7, for example, this embodiment provides a fluid path that includes at least three turns effectively of 90° as the fluid enters from the top, passes through the base and then exits through the top of the projection. It is understood that this is a preferred embodiment only and that other angles or additional angular deviations in the path can also be incorporated into the fluid path as desired to achieve a certain spray geometry. For example, angles of any size can be utilized including any acute or obtuse angle, and not limited to angles of approximately 15°, 30°, 45°, 60°, 75°, 105°, 120°, 135°, 150°, 165° and combinations thereof.

Figure 5:
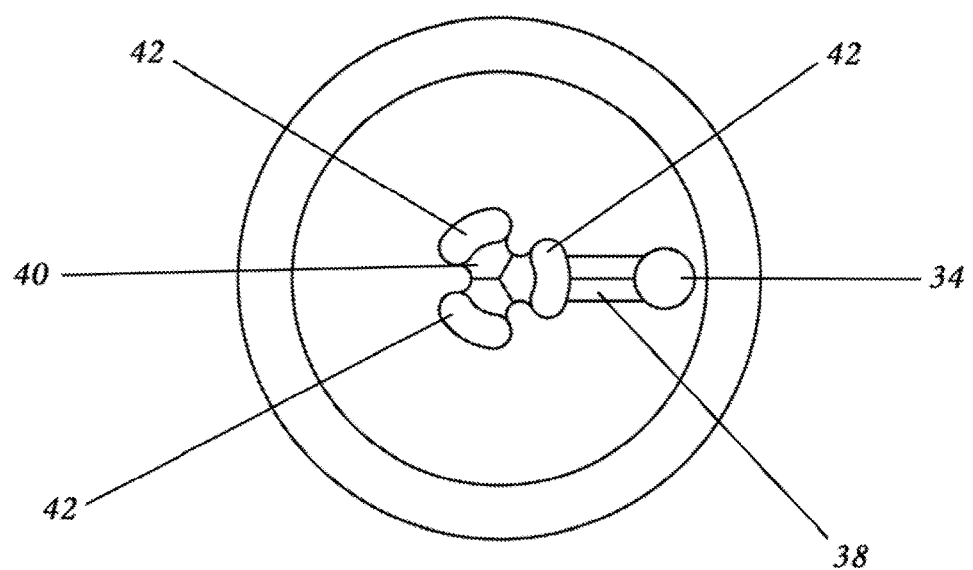
Figure 6:
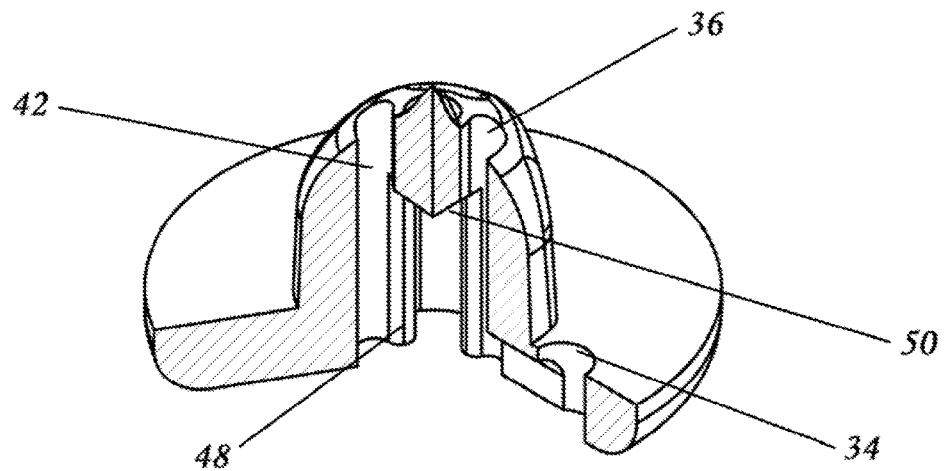
Figure 6:
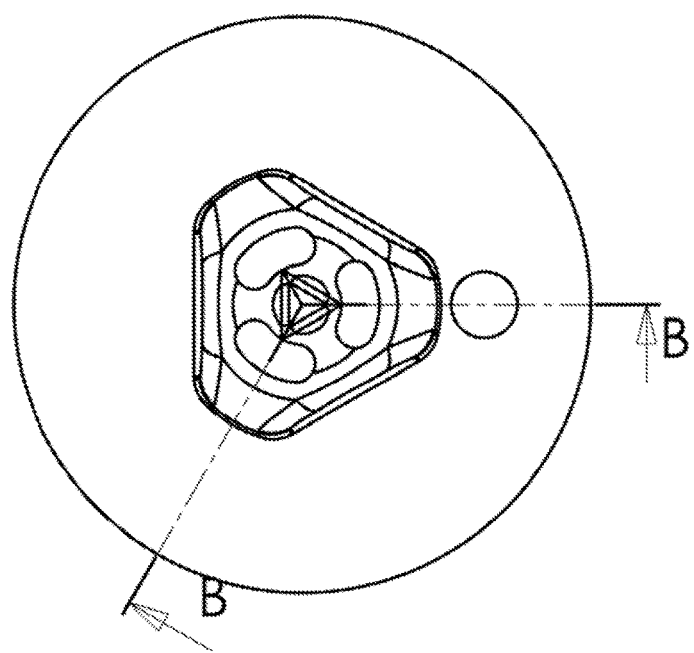
Figure 10:
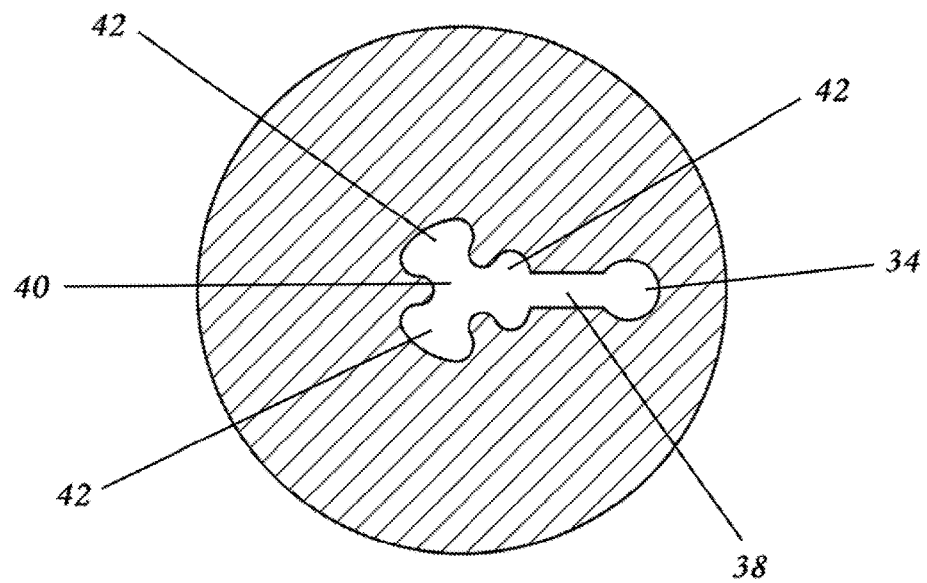
Figure 10:
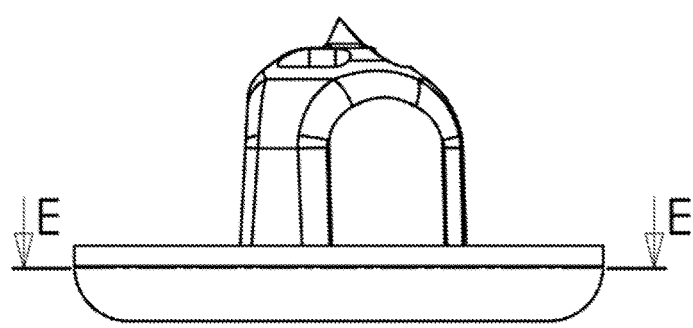

In the embodiment shown, three outlets are provided. The base 12 and projection 14 provide a fluid path from the interior of a blister containing the piercer into and through the base and into a central cavity 40 as shown in FIGS. 5, 7 and 10, and out through the outlet channels 42 and openings 36. The interior channel or cavity provides structures that create turbulence in a liquid that is flowing through the cavity under pressure. In the embodiment shown in the figures the fluid path includes an conduit 38 from the inlet opening 34 into the interior cavity. The cavity includes a central channel 40 and three tubular side channels 42 that lead to the three outlet openings 36 respectively. As best seen in FIG. 6, the three tubular channels are connected by angular walls 48 that form the central cavity, and the top of the cavity is formed by an inverse pyramidal configuration 50, the surfaces of which deflect the liquid flow into the three side channels. This combination of angled surfaces creates turbulence in the fluid flow as the fluid flows from the internal cavity into the delivery channels and produces the desired spray geometry for liquids expelled through the piercer.

The top, or most distal end of the projection provides a piercing point or lancet 16, effective to pierce the lidstock of a blister when forced against it, as when a blister containing the piercer is crushed to dispense the contents. The size and orientation of the lancet is designed to minimize any potential interference with the spray by any flap formed in the lidstock as it is pierced by the lancet. The embodiment shown in the figures has a triangular pyramid shape with 3 bilobal discharge ports disposed around the base. It is understood that other configurations are also contemplated including, but not limited to 2, 4, 5, or six channels for example, which may be used for dispensing fluids to different parts of a user's body or for alternate non-medical uses.

During use, a piercing device as described herein can be placed in a formed blister as a step in the production of a measured dosage form. The production step can be described in certain embodiments as a process for manufacturing a shaped article for unit-dose packaging with at least one formed recess, that includes (a) holding a film between at least one retaining tool and at least one die, wherein the die has at least one die opening defined by a substantially circular edge of the die opening; (b) driving a first plunger into the die opening, which causes the film to be formed into a primary contour, the contour having a depth of at least about 100% and up to about 150% of the depth of the final formed recess, and an Area Ratio of from greater than 1.1, 1.2, 1.3, 1.5 or 2.1) to about 3.0; (c) driving a second plunger into the primary contour to a depth that is less than the depth of the primary contour, wherein the second plunger forms a second geometric shape with substantially the same Area Ratio as the primary contour, the second geometric shape comprising a portion distal from the die opening edge that is sized to fit a base portion of an internal piercer comprising a base portion and a piercing tip; and (d) inserting an internal piercer into the formed recess, wherein the base portion of the internal piercer is positioned in the shape formed in the distal portion of the formed recess by the second plunger. The dosage form can then be filled with a measured quantity of a liquid or powder composition and sealed, all within a sterile cabinet, room or machine.

The formed blister, either individually or in a multiple blister pack or strip, is placed in a dispensing device. In certain embodiments a dispensing device can be described as typically including a body with a nozzle end for directing a spray or mist into the eye, ear, nose or throat of a user, a trigger device to be operated by a user, a dosage form, a cavity to contain the dosage form as described herein, a plunger or piston body, an actuator mechanism linking the trigger device to the plunger, a piercing mechanism positioned to pierce the dosage form upon activation of the trigger, and a discharge channel to release a spray of the liquid composition through the nozzle in a predetermined spray plume geometry and direction. In certain embodiments the trigger mechanism can include a mechanical advantage, a mechanical disadvantage or both, or the system may be fired by an electromechanical mechanism in order to ensure that the device can be operated by a person with limited strength, and also to ensure that the blister is crushed with sufficient force to dispense the contents in the desired spray geometry.

All of the devices and methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

The invention claimed is:

1. A piercing device for delivering a predetermined quantity of a flowable liquid or powder contained in a crushable blister into a spray, plume, stream or droplets, said device comprising:
   a base comprising a top;
   a substantially hollow, elongated member extending from the base and comprising a body region and terminating in a lancet piercing tip region;
   the lancet piercing tip region comprising a tip and a base end;
   an internal delivery channel formed by the hollow interior of the elongated member extending from the base and terminating in a plurality of discharge ports arranged around the base end of piercing tip region;
   wherein the internal delivery channel comprises:
   a central cavity; and
   a plurality of outlet channels radially disposed around the central cavity and open to the central cavity along at least a portion of an innermost side of each outlet channel and wherein each outlet channel terminates in one of the plurality of discharge ports,
   wherein the central cavity is defined by angular walls disposed between the outlet channels and an angular top surface proximate the tip configured to deflect fluid from the central cavity into the outlet channels when the fluid enters one or more conduits under pressure;
   one or more inlet ports in the base in fluid communication with an interior of the crushable blister, and
   the one or more conduits providing fluid communication between the one or more inlet ports and the internal delivery channel.

2. The piercing device of claim 1, wherein at least one of the conduits from an inlet port to the internal delivery channel comprises one or more bends or turns.

3. The piercing device of claim 2, wherein one or more of the bends or turns is an angle of from 20° to 135°.

4. The piercing device of claim 2, wherein at least one of the conduits from an inlet port to the internal delivery channel comprises one or more 90° turns.

5. The piercing device of claim 1, wherein the internal delivery channel comprises three outlet channels disposed radially around the central cavity and each terminating in one of three discharge ports disposed radially around the base end of the piercing tip region.

6. The piercing device of claim 1, wherein the piercing tip region is configured as a three sided pyramid.

7. The piercing device of claim 1, wherein during use, delivery of a fluid that enters said one or more inlet ports under pressure, creates a laminar flow as the fluid flows through the one or more conduits and creates a turbulent flow as the fluid flows into and through the internal delivery channel and one or more of said plurality of outlet channels, such that the fluid is released through the discharge ports as a spray or mist.

8. A dosage form containing the piercing device of claim 1 and a liquid or powder composition.

9. The dosage form of claim 8, wherein the liquid or powder composition is a medical composition.

10. The dosage form of claim 9, wherein the liquid or powder composition is a medical composition for administration to the eye, ear, nasal passage or topical area of a user.

11. The dosage form of claim 9, wherein the liquid or powder composition is a medical composition for administration to the eye of a user.

12. The dosage form of claim 8, wherein the dosage form contains a volume of from 1 µl to 50 µl of flowable liquid or powder.

13. The dosage form of claim 8, wherein the dosage form contains a volume of from 75 µl to 500 µl of flowable liquid or powder.

14. The dosage form of claim 8, wherein the dosage form contains a volume of from 1 µl to 1000 µl of flowable liquid or powder.

15. The dosage form of claim 8, wherein the outlet channels and discharge ports have a bilobal cross section.

16. An internally pierced dosage form comprising: a modified dome shaped blister with a circular base; a planar sheet of pierceable material sealed to the base of the blister; and an internal chamber contained within the blister and the planar sheet; a piercing device and a medical composition contained in the internal chamber; and wherein the piercing device comprises:
   a base comprising a top;
   a substantially hollow, elongated member extending from the base and comprising a body region and terminating in a lancet piercing tip region;

wherein the lancet piercing tip region comprises a base end;
an internal delivery channel formed by the hollow interior of the elongated member extending from the base and terminating in a plurality of discharge ports arranged around the base end of the piercing tip region;
one or more inlet ports in the base in fluid communication with the interior of the crushable blister; and
one or more conduits providing fluid communication between the one or more inlet ports and the internal delivery channel.

17. The internally pierced dosage form of claim 16, wherein the internal delivery channel comprises:
a central cavity extending from, and in fluid communication with the one or more conduits, and
a plurality of outlet channels radially disposed around the central cavity and open to the central cavity along at least a portion of an innermost side of each outlet channel and wherein each outlet channel terminates in one of said plurality of discharge ports,
wherein the central cavity is defined by angular walls disposed between the outlet channels and an angular top surface proximate the lancet piercing tip region configured to deflect a fluid from the central cavity into the outlet channels when the fluid enters the internal delivery channel under pressure.

18. The internally pierced dosage form of claim 16, wherein at least one of the conduits from an inlet port to the internal delivery channel comprises one or more bends or turns.

19. The internally pierced dosage form of claim 18, wherein one or more of the bends or turns is an angle of from 20° to 135°.

20. The internally pierced dosage form of claim 18, wherein at least one of the conduits from an inlet port to the internal delivery channel comprises one or more 90° turns.

21. The internally pierced dosage form of claim 16, comprising three outlet channels disposed radially around the central cavity and each terminating in one of three discharge ports disposed radially around the base end of the piercing tip region.

22. The internally pierced dosage form of claim 16, wherein the piercing tip region is configured as a three sided pyramid.

23. The internally pierced dosage form of claim 17, wherein during use, delivery of a fluid that enters said one or more inlet ports under pressure, creates a laminar flow as a fluid flows through the one or more conduits and creates a turbulent flow as the fluid flows into and through the internal delivery channel and outlet channels, such that the fluid is released through the discharge ports as a spray or mist.

24. The internally pierced dosage form of claim 16, wherein the medical composition is a fluid composition for administration to the eye, ear, nasal passage or topical area of a user.

25. The internally pierced dosage form of claim 16, wherein the medical composition is a fluid composition for administration to the eye of a user.

26. The internally pierced dosage form of claim 16, wherein the dosage form contains a volume of from 1 µl to 50 µl of flowable liquid or powder.

27. The internally pierced dosage form of claim 16, wherein the dosage form contains a volume of from 75 µl to 500 µl of flowable liquid or powder.

28. The internally pierced dosage form of claim 16, wherein the dosage form contains a volume of from 1 µl to 1000 µl of flowable liquid or powder.

29. The internally pierced dosage form of claim 17, wherein the outlet channels and discharge ports have a bilobal cross section.

30. A piercing device for delivering a predetermined quantity of a flowable liquid or powder contained in a crushable blister into a spray, plume, stream or droplets, said device comprising:
a base comprising a top and one or more inlet ports in fluid communication with the interior of the crushable blister;
a substantially hollow, elongated member extending from the base and comprising a body region and terminating in a lancet piercing tip region, wherein the lancet piercing tip region comprises a base end;
an internal delivery channel formed by the hollow interior of the elongated member extending from the base and terminating in a plurality of bilobal discharge ports arranged around the base end of the lancet piercing tip region, said internal delivery channel comprising a central cavity extending from, and in fluid communication with one or more inlet ports, and a plurality of bilobal shaped outlet channels radially disposed around the central cavity and open to the central cavity along at least a portion of an innermost side of each outlet channel and each outlet channel terminating in one of said bilobal discharge ports, wherein the central cavity is defined by angular walls disposed between the outlet channels and an angular top surface proximate the piercing tip region configured to deflect fluid from the central cavity into the outlet channels when the fluid enters the inlet ports under pressure; and
one or more conduits providing fluid communication between the one or more inlet ports and the internal delivery channel.

31. A piercing device for delivering a predetermined quantity of a flowable liquid or powder contained in a crushable blister into a spray, plume, stream or droplets, said device comprising:
a base comprising a top and one or more inlet ports in fluid communication with an interior of the crushable blister and each of said one or more inlet ports in fluid communication with an internal delivery channel through a conduit;
a substantially hollow, elongated member extending from the base and comprising a body region and terminating in a lancet piercing tip region configured as a three sided pyramid; and
the lancet piercing tip region comprising a base end;
wherein the internal delivery channel is formed by the hollow interior of the elongated member, said internal delivery channel comprising a central cavity extending from the base and three outlet channels having bilobal cross sections radially disposed around the central cavity and open to the central cavity along at least a portion of an innermost side of each outlet channel and each outlet channel terminating in one of said three discharge ports each having a bilobal cross section and radially disposed around the base end of the lancet piercing tip region, wherein the central cavity is defined by angular walls disposed between the outlet channels and an angular top surface proximate the lancet piercing tip region configured to deflect fluid from the central cavity into the outlet channels when the fluid enters the one or more inlet ports under pressure.

\* \* \* \* \*